United States Patent
Krumm et al.

(10) Patent No.: US 11,259,856 B2
(45) Date of Patent: Mar. 1, 2022

(54) COMBINATION ULTRASONIC AND ELECTROSURGICAL INSTRUMENT AND METHOD FOR SEALING TISSUE IN SUCCESSIVE PHASES

(71) Applicant: Ethicon LLC, Guaynabo, PR (US)

(72) Inventors: Amy M. Krumm, Cincinnati, OH (US); Ashvani K. Madan, Mason, OH (US)

(73) Assignee: Cilag GmbH International, Zug (CH)

( * ) Notice: Subject to any disclaimer, the term of this patent is extended or adjusted under 35 U.S.C. 154(b) by 631 days.

(21) Appl. No.: 15/967,784

(22) Filed: May 1, 2018

(65) Prior Publication Data

US 2018/0333190 A1    Nov. 22, 2018

Related U.S. Application Data (60) Provisional application No. 62/509,336, filed on May 22, 2017.

(51) Int. Cl.
*A61B 18/14*    (2006.01)
*A61B 18/00*    (2006.01)
(Continued)

(52) U.S. Cl.
CPC ...... *A61B 18/00* (2013.01); *A61B 17/320092* (2013.01); *A61B 18/1233* (2013.01);
(Continued)

(58) Field of Classification Search
CPC .... A61B 17/320068; A61B 17/320092; A61B 18/00; A61B 18/1233; A61B 18/1442;
(Continued)

(56) References Cited

U.S. PATENT DOCUMENTS 5,322,055 A    6/1994 Davison et al.
5,792,135 A    8/1998 Madhani et al.
(Continued)

FOREIGN PATENT DOCUMENTS

EP    1 839 599 A1    10/2007

OTHER PUBLICATIONS

International Search Report and Written Opinion for International Application No. PCT/US2018/033301, dated Jul. 30, 2018, 13 pgs.
(Continued)

*Primary Examiner* — Khadijeh A Vahdat
(74) *Attorney, Agent, or Firm* — Frost Brown Todd LLC (57) ABSTRACT

An ultrasonic surgical instrument and method of sealing a tissue includes generating a desired burst pressure in the tissue, sealing the tissue, verifying that the tissue is sealed with further application of at least one of the ultrasonic energy and the RF energy. The ultrasonic surgical instrument further includes an end effector having an ultrasonic blade, an RF electrode, and a controller. The controller operatively connects to the ultrasonic blade and the RF electrode and is configured to direct application of ultrasonic and RF energies according to an initial phase, a power phase, and a termination phase for respectively generating a desired burst pressure in the tissue, sealing the tissue, and verifying the sealing of the tissue while inhibiting transection of the tissue.

20 Claims, 8 Drawing Sheets

(51) Int. Cl.
- *A61B 17/32* (2006.01)
- *A61B 18/12* (2006.01)
- *A61B 17/00* (2006.01)
- *A61B 90/00* (2016.01)

(52) U.S. Cl.
CPC .. *A61B 18/1445* (2013.01); *A61B 2017/0019* (2013.01); *A61B 2017/00026* (2013.01); *A61B 2017/00084* (2013.01); *A61B 2017/00106* (2013.01); *A61B 2017/00526* (2013.01); *A61B 2017/320075* (2017.08); *A61B 2017/320088* (2013.01); *A61B 2017/320094* (2017.08); *A61B 2017/320095* (2017.08); *A61B 2018/0063* (2013.01); *A61B 2018/00607* (2013.01); *A61B 2018/00642* (2013.01); *A61B 2018/00648* (2013.01); *A61B 2018/00654* (2013.01); *A61B 2018/00672* (2013.01); *A61B 2018/00678* (2013.01); *A61B 2018/00702* (2013.01); *A61B 2018/00708* (2013.01); *A61B 2018/00714* (2013.01); *A61B 2018/00755* (2013.01); *A61B 2018/00761* (2013.01); *A61B 2018/00779* (2013.01); *A61B 2018/00875* (2013.01); *A61B 2018/00916* (2013.01); *A61B 2018/00928* (2013.01); *A61B 2018/00994* (2013.01); *A61B 2018/126* (2013.01); *A61B 2018/1452* (2013.01); *A61B 2090/064* (2016.02)

(58) Field of Classification Search
CPC ...... A61B 18/1445; A61B 2017/00026; A61B 2017/00084; A61B 2017/00106; A61B 2017/0019; A61B 2017/00526; A61B 2017/320075; A61B 2017/320088; A61B 2017/320094; A61B 2017/320095; A61B 2018/00678; A61B 2018/0063; A61B 2018/00642; A61B 2018/00648; A61B 2018/00654; A61B 2018/00672; A61B 2018/00702; A61B 2018/00708; A61B 2018/00714; A61B 2018/00755; A61B 2018/00761; A61B 2018/00779; A61B 2018/00791; A61B 2018/00845; A61B 2018/00875; A61B 2018/0088; A61B 2018/00916; A61B 2018/00928; A61B 2018/00994; A61B 2018/126; A61B 2018/1452; A61B 2018/1457; A61B 2018/1467; A61B 2090/064
USPC ..................................................... 606/41–52
See application file for complete search history.

(56) References Cited

U.S. PATENT DOCUMENTS

| | | |
|---|---|---|
| 5,817,084 A | 10/1998 | Jensen |
| 5,873,873 A | 2/1999 | Smith et al. |
| 5,878,193 A | 3/1999 | Wang et al. |
| 5,980,510 A | 11/1999 | Tsonton et al. |
| 6,231,565 B1 | 5/2001 | Tovey et al. |
| 6,283,981 B1 | 9/2001 | Beaupre et al. |
| 6,309,400 B2 | 10/2001 | Beaupre |
| 6,325,811 B1 | 12/2001 | Messerly |
| 6,364,888 B1 | 4/2002 | Niemeyer et al. |
| 6,423,082 B1 | 7/2002 | Houser et al. |
| 6,500,176 B1 | 12/2002 | Truckai et al. |
| 6,773,444 B2 | 8/2004 | Messerly |
| 6,783,524 B2 | 8/2004 | Anderson et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,524,320 B2 | 4/2009 | Tierney et al. |
| 7,691,098 B2 | 4/2010 | Wallace et al. |
| 7,806,891 B2 | 10/2010 | Nowlin et al. |
| 8,057,498 B2 | 11/2011 | Robertson |
| 8,058,771 B2 | 11/2011 | Giordano et al. |
| 8,366,727 B2 | 2/2013 | Witt et al. |
| 8,460,326 B2 | 6/2013 | Houser et al. |
| 8,461,744 B2 | 6/2013 | Wiener et al. |
| 8,479,969 B2 | 7/2013 | Shelton, IV |
| 8,573,461 B2 | 11/2013 | Shelton, IV et al. |
| 8,573,465 B2 | 11/2013 | Shelton, IV |
| 8,591,536 B2 | 11/2013 | Robertson |
| 8,602,288 B2 | 12/2013 | Shelton, IV et al. |
| 8,616,431 B2 | 12/2013 | Timm et al. |
| 8,623,027 B2 | 1/2014 | Price et al. |
| 8,663,220 B2 | 3/2014 | Wiener et al. |
| 8,783,541 B2 | 7/2014 | Shelton, IV et al. |
| 8,800,838 B2 | 8/2014 | Shelton, IV |
| 8,820,605 B2 | 9/2014 | Shelton, IV et al. |
| 8,844,789 B2 | 9/2014 | Shelton, IV et al. |
| 8,939,974 B2 | 1/2015 | Boudreaux et al. |
| 9,044,261 B2 | 6/2015 | Houser |
| 9,089,327 B2 | 7/2015 | Worrell et al. |
| 9,161,803 B2 | 10/2015 | Yates et al. |
| 9,192,431 B2 | 11/2015 | Woodruff et al. |
| 9,237,921 B2 | 1/2016 | Messerly et al. |
| 9,301,759 B2 | 4/2016 | Spivey et al. |
| 9,402,682 B2 | 8/2016 | Worrell et al. |
| 9,439,668 B2 | 9/2016 | Timm et al. |
| 9,545,253 B2 | 1/2017 | Worrell et al. |
| 9,572,622 B2 | 2/2017 | Shelton, IV et al. |
| 9,681,884 B2 | 6/2017 | Clem et al. |
| 9,724,118 B2 | 8/2017 | Schulte et al. |
| 10,194,972 B2 | 2/2019 | Yates et al. |
| 10,617,463 B2 | 4/2020 | McHenry et al. |
| 10,813,684 B2 | 10/2020 | Worrell et al. |
| 2011/0087212 A1 | 4/2011 | Aldridge et al. |
| 2012/0078243 A1 | 3/2012 | Worrell et al. |
| 2012/0116391 A1 | 5/2012 | Houser et al. |
| 2015/0141981 A1 | 5/2015 | Price et al. |
| 2015/0257780 A1 | 9/2015 | Houser et al. |
| 2016/0022305 A1 | 1/2016 | Lamping et al. |
| 2016/0270840 A1 | 9/2016 | Yates et al. |
| 2017/0000516 A1 | 1/2017 | Stulen et al. |
| 2017/0000541 A1 | 1/2017 | Yates et al. |
| 2017/0000542 A1 | 1/2017 | Yates et al. |
| 2017/0000554 A1 | 1/2017 | Yates et al. |
| 2017/0056056 A1 | 3/2017 | Wiener et al. |

OTHER PUBLICATIONS

International Search Report and Written Opinion for International Application No. PCT/US2018/033303, dated Jan. 24, 2019, 20 pgs.
U.S. Appl. No. 62/509,336, entitled "Control Algorithm for Surgical Instrument With Ultrasonic and Electrosurgical Modalities," filed May 22, 2017.
International Search Report and Written Opinion for International Application No. PCT/US2018/033305, dated Aug. 23, 2018, 16 pages.
International Search Report and Written Opinion for International Application No. PCT/US2018/033306, dated Sep. 3, 2018, 17 pages.
International Search Report and Written Opinion for International Application No. PCT/US2018/033309, dated Aug. 17, 2018, 16 pages.
International Search Report and Written Opinion for International Application No. PCT/US2018/033311, dated Aug. 23, 2018, 16 pages.
U.S. Appl. No. 15/967,740, entitled "Combination Ultrasonic and Electrosurgical Instrument Having Electrical Circuits with Shared Return Path," filed May 1, 2018.

(56) References Cited

OTHER PUBLICATIONS

U.S. Appl. No. 15/967,746, entitled "Combination Ultrasonic and Electrosurgical Instrument Having Slip Ring Electrical Contact Assembly," filed May 1, 2018.
U.S. Appl. No. 15/967,747, entitled "Combination Ultrasonic and Electrosurgical Instrument Having Electrically Insulating Features," filed May 1, 2018.
U.S. Appl. No. 15/967,751, entitled "Combination Ultrasonic and Electrosurgical Instrument Having Curved Ultrasonic Blade," filed May 1, 2018.
U.S. Appl. No. 15/967,753, entitled "Combination Ultrasonic and Electrosurgical Instrument Having Clamp Arm Electrode," filed May 1, 2018.
U.S. Appl. No. 15/967,758, entitled "Combination Ultrasonic and Electrosurgical Instrument with Clamp Arm Position Input and Method for Identifying Tissue State," filed May 1, 2018.
U.S. Appl. No. 15/967,759, entitled "Combination Ultrasonic and Electrosurgical Instrument Having Ultrasonic Waveguide with Distal Overmold Member," filed May 1, 2018.
U.S. Appl. No. 15/967,761, entitled "Combination Ultrasonic and Electrosurgical System Having Generator Filter Circuitry," filed May 1, 2018.
U.S. Appl. No. 15/967,763, entitled "Combination Ultrasonic and Electrosurgical Instrument with a Production Clamp Force Based Ultrasonic Seal Process and Related Methods," filed May 1, 2018.
U.S. Appl. No. 15/967,764, entitled "Combination Ultrasonic and Electrosurgical System Having EEPROM and ASIC Components," filed May 1, 2018.
U.S. Appl. No. 15/967,770, entitled "Combination Ultrasonic and Electrosurgical Instrument with a Production Clamp Force Based Ultrasonic Seal Process and Related Methods," filed May 1, 2018.
U.S. Appl. No. 15/967,775, entitled "Combination Ultrasonic and Electrosurgical Instrument with Adjustable Energy Modalities and Method for Limiting Blade Temperature," filed May 1, 2018.
U.S. Appl. No. 15/967,777, entitled "Combination Ultrasonic and Electrosurgical Instrument and Method for Sealing Tissue with Various Termination Parameters," filed May 1, 2018.
U.S. Appl. No. 62/509,351, entitled "Ultrasonic Instrument with Electrosurgical Features," filed May 22, 2017.
U.S. Appl. No. 15/967,758.
U.S. Appl. No. 15/967,763.
U.S. Appl. No. 15/967,770.
U.S. Appl. No. 15/967,775.
U.S. Appl. No. 15/967,777.
European Examination Report dated Jun. 28, 2021 for Application No. EP 18729278.4, 4 pgs.
European Examination Report dated Jun. 29, 2021 for Application No. EP 18731583.3, 4 pgs.
European Examination Report dated Jun. 29, 2021 for Application No. EP 18731584.1, 4 pgs.
European Examination Report dated Jun. 30, 2021 for Application No. EP 18731585.8, 4 pgs.

COMBINATION ULTRASONIC AND ELECTROSURGICAL INSTRUMENT AND METHOD FOR SEALING TISSUE IN SUCCESSIVE PHASES

CROSS-REFERENCE TO RELATED APPLICATION

This application claims priority to U.S. Provisional Pat. App. No. 62/509,336, entitled "Control Algorithm for Surgical Instrument with Ultrasonic and Electrosurgical Modalities," filed May 22, 2017, the disclosure of which is incorporated by reference herein.

BACKGROUND

Ultrasonic surgical instruments utilize ultrasonic energy for both precise cutting and controlled coagulation. Ultrasonic energy cuts and coagulates by vibrating a blade in contact with tissue. Vibrating at frequencies of approximately 55.5 kilohertz (kHz), for example, the ultrasonic blade denatures protein in the tissue to form a sticky coagulum. Pressure exerted on the tissue with the blade surface collapses blood vessels and allows the coagulum to form a hemostatic seal. The precision of cutting and coagulation may be controlled by the surgeon's technique and adjusting the power level, blade edge, tissue traction, and blade pressure, for example.

Examples of ultrasonic surgical devices include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; U.S. Pat. No. 8,623,027, entitled "Ergonomic Surgical Instruments," issued Jan. 7, 2014, the disclosure of which is incorporated by reference herein; and U.S. Pub. No. 2016/0022305, entitled "Ultrasonic Blade Overmold," published Jan. 28, 2016, issued as U.S. Pat. No. 9,750,521 on Sep. 5, 2017, the disclosure of which is incorporated by reference herein.

Electrosurgical instruments utilize electrical energy for sealing tissue, and generally include a distally mounted end effector that can be configured for bipolar or monopolar operation. During bipolar operation, electrical current is provided through the tissue by active and return electrodes of the end effector. During monopolar operation, current is provided through the tissue by an active electrode of the end effector and a return electrode (e.g., a grounding pad) separately located on a patient's body. Heat generated by the current flowing through the tissue may form hemostatic seals within the tissue and/or between tissues, and thus may be particularly useful for sealing blood vessels, for example. The end effector of an electrosurgical device may also include a cutting member that is movable relative to the tissue and the electrodes to transect the tissue.

Electrical energy applied by an electrosurgical device can be transmitted to the instrument by a generator coupled with the instrument. The electrical energy may be in the form of radio frequency ("RF") energy, which is a form of electrical energy generally in the frequency range of approximately 300 kilohertz (kHz) to 1 megahertz (MHz). In use, an electrosurgical device can transmit such energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy works particularly well on connective tissue, which is primarily comprised of collagen and shrinks when contacted by heat.

An example of an RF electrosurgical device is the ENSEAL® Tissue Sealing Device by Ethicon Endo-Surgery, Inc., of Cincinnati, Ohio. Further examples of electrosurgical devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical devices and related concepts are disclosed in U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; U.S. Pat. No. 9,161,803, entitled "Motor Driven Electrosurgical Device with. Mechanical and Electrical Feedback," issued Oct. 20, 2015, the disclosure of which is incorporated by reference herein; U.S. Pub. No. 2012/0078243, entitled "Control Features for Articulating Surgical Device," published Mar. 29, 2012, issued as U.S. Pat. No. 9,877,720 on Jan. 30, 2018, the disclosure of which is incorporated by reference herein; U.S. Pat. No. 9,402,682, entitled "Articulation Joint Features for Articulating Surgical Device," issued Aug. 2, 2016, the disclosure of which is incorporated by reference herein; U.S. Pat. No. 9,089,327, entitled "Surgical Instrument with Multi-Phase Trigger Bias," issued Jul. 28, 2015, the disclosure of which is incorporated by reference herein; U.S. Pat. No. 9,545,253, entitled "Surgical Instrument with Contained Dual Helix Actuator Assembly," issued Jan. 17, 2017, the disclosure of which is incorporated by reference herein; and U.S. Pat. No. 9,572,622, entitled "Bipolar Electrosurgical Features for Targeted Hemostasis," issued Feb. 21, 2017, the disclosure of which is incorporated by reference herein.

Some instruments may provide ultrasonic and RF energy treatment capabilities through a single surgical device. Examples of such devices and related methods and concepts are disclosed in U.S. Pat. No. 8,663,220, entitled "Ultrasonic Surgical Instruments," issued Mar. 4, 2014, the disclosure of which is incorporated by reference herein; U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and U.S. Pub. No. 2017/0000541, entitled "Surgical Instrument with User Adaptable Techniques," published Jan. 5, 2017, issued as U.S. Pat. No. 11,141,213 on Oct. 12, 2021, the disclosure of which is incorporated by reference herein.

While various types of ultrasonic surgical instruments and electrosurgical instruments, including combination ultrasonic-electrosurgical devices, have been made and used, it is believed that no one prior to the inventor(s) has made or used the invention described herein.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical System

Figure 1:
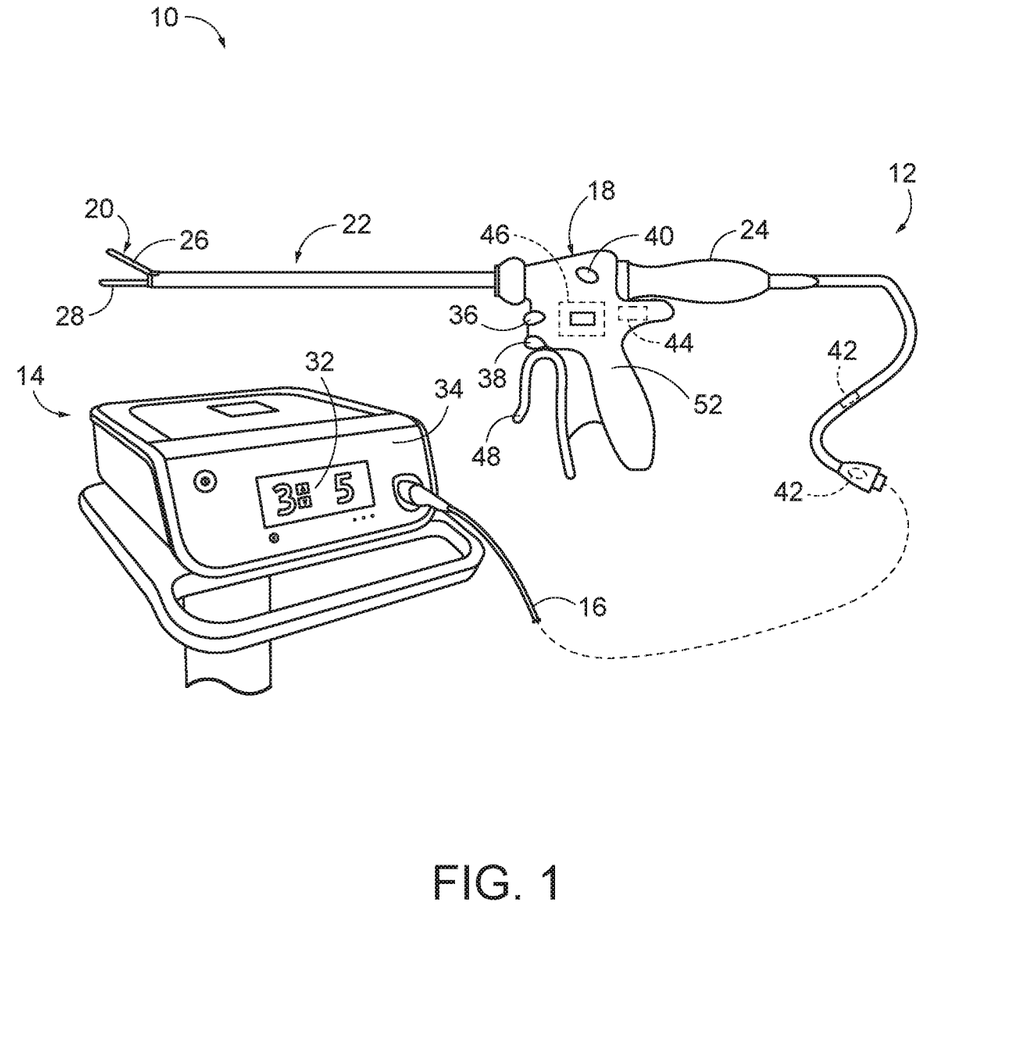
FIG. 1 depicts a schematic view of an exemplary ultrasonic surgical instrument including a shaft assembly and a handle assembly operatively connected to an ultrasonic generator.

FIG. 1 illustrates one example of a surgical system (10) including a surgical instrument (12) and a generator (14) coupled via a cable (16). Surgical instrument (12) has a proximally positioned handle assembly (18), which may also be referred to as a handpiece, a distally positioned end effector (20), a shaft assembly (22) extending therebetween, and an ultrasonic transducer (24). End effector (20) generally includes a clamp arm (26) pivotally connected relative to an ultrasonic blade (28) and configured to pivot from an open position of an open configuration to a closed position of a closed configuration as discussed below in greater detail. Ultrasonic blade (28) is acoustically coupled with ultrasonic transducer (24) via an acoustic waveguide (not shown) for providing ultrasonic energy to ultrasonic blade (28). In addition, end effector (20) further includes a plurality of RF electrodes (30) positioned therealong for contacting the tissue in either the open or closed position as desired by a clinician. Generator (14) operatively connects to ultrasonic blade (28) and RF electrodes (30) to respectively provide ultrasonic energy and RF energy to ultrasonic blade (28) and RF electrodes (30) to thereby cut and/or seal the tissue is use.

In some versions, clamp arm (26) has two or more electrodes (30). In some such versions, electrodes (30) of clamp arm are capable of applying bipolar RF energy to tissue. In some such versions, ultrasonic blade (28) remains electrically neutral, such that ultrasonic blade (28) is not part of the RF circuit. In some other versions, ultrasonic blade (28) forms part of the RF circuit, such that ultrasonic blade (28) cooperates with one or more electrodes (30) of clamp arm (26) to apply bipolar RF energy to tissue. By way of example only, some versions of clamp arm (26) may have just one electrode (30) that serves as an active pole for RF energy; while ultrasonic blade (28) provides a return pole for RF energy. Thus, the term "electrodes (30)" should be read to include versions where clamp arm (26) has only one single electrode.

It should be understood that terms such as "proximal" and "distal" are used herein with reference to surgical instrument (12). Thus, end effector (20) is distal with respect to the more proximal handle assembly (18). It will be further appreciated that for convenience and clarity, spatial terms such as "upper" and "lower" are used herein with respect to the drawings. However, surgical instruments are used in many orientations and positions, and these terms are not intended to be limiting and absolute. Likewise, terms such as "instrument" and "device" as well as "limit" and "cap" may be used interchangeably.

A. Exemplary Generator

With reference to FIG. 1, generator (14) drives a combination surgical instrument (12) with both ultrasonic and RF energies. Generator (14) is shown separate from surgical instrument (12) in the present example, but, alternatively, generator (14) may be formed integrally with surgical instrument (12) to form a unitary surgical system. Generator (14) generally includes an input device (32) located on a front panel (34) of generator (14). Input device (32) may have any suitable device that generates signals suitable for programming the operation of generator (32). For example, in operation, the clinician may program or otherwise control operation of generator (32) using input device (32) (e.g., by one or more processors contained in the generator) to control the operation of generator (14) (e.g., operation of the ultrasonic generator drive circuit (not shown) and/or RF generator drive circuit (not shown)).

In various forms, input device (32) includes one or more buttons, switches, thumbwheels, keyboard, keypad, touch screen monitor, pointing device, remote connection to a general purpose or dedicated computer. In other forms, input device (32) may having a suitable user interface, such as one or more user interface screens displayed on a touch screen monitor. Accordingly, the clinician may selectively set or program various operating parameters of the generator, such as, current (I), voltage (V), frequency (f), and/or period (T) of a drive signal or signals generated by the ultrasonic and RF generator drive circuits (not shown). Specifically, in the present example, generator (32) is configured to deliver various power states to the surgical instrument (10) that include, but are not necessarily limited to, only ultrasonic energy, only RF energy, and a combination of ultrasonic and RF energies, which simultaneously powers ultrasonic blade (28) and RF electrodes (30). It will be appreciated that input device (32) may have any suitable device that generates signals suitable for programming the operation of generator (14) and should not be unnecessarily limited to input device (32) shown and described herein.

By way of example only, generator (14) may comprise a GEN04 or GEN11 sold by Ethicon Endo-Surgery, Inc. of Cincinnati, Ohio. In addition, or in the alternative, generator (14) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein.

B. Exemplary Surgical Instrument

Surgical instrument (10) of the present example shown in FIG. 1 includes a plurality of energy inputs, which are more particularly referred to herein as an upper button (36), lower button (38), and side button (40). By way of example, upper button (36) is configured to direct generator (14) to power ultrasonic transducer (24) with a maximum ultrasonic energy output, whereas lower button (38) is configured to direct generator (14) to power ultrasonic transducer (24) with a lower ultrasonic energy output. By way of further example, side button (40) is configured to direct generator (14) to power ultrasonic transducer (24) with a pulsed energy output, such as 5 continuous signals and 5 or 4 or 3 or 2 or 1 pulsed signals. In one or more examples, the specific drive signal configuration directed by energy inputs may be controlled and/or based upon EEPROM settings in generator (14) and/or user power level selection(s). By way of further example, surgical instrument (10) may include a two-button configuration for selectively directing ultrasonic and RF energies as described herein. Various examples of instruments having two-button input configurations are described in various patent references cited herein. In any case, it will be appreciated that the invention described herein is not intended to be unnecessarily limited to a particular input button, switch, etc. to the extent that any form of input may be so used.

Surgical instrument (12) further includes a first data circuit (42) and a second data circuit (44) in communication with generator (14). For example, first data circuit (42) indicates a burn-in frequency slope. Additionally or alternatively, any type of information may be communicated to second data circuit (42) for storage therein via a data circuit interface (e.g., using a logic device). Such information may comprise, for example, an updated number of operations in which surgical instrument (12) has been used and/or dates and/or times of its usage. In other examples, second data circuit (44) may transmit data acquired by one or more sensors (e.g., an instrument-based temperature sensor). In still other examples, second data circuit (44) may receive data from generator (14) and provide an indication to a clinician (e.g., an LED indication or other visible indication) based on the received data to and/or from surgical instrument (12). In the present example, second data circuit (44) stores information about the electrical and/or ultrasonic properties of an associated transducer (24) and/or end effector (20), which includes data measured and collected from ultrasonic blade (28) and/or RF electrodes (30).

To this end, various processes and techniques described herein are performed by a controller (46), which includes internal logic. In one example, controller (46) has at least one processor and/or other controller device in communication with generator (14), ultrasonic blade (28), RF electrodes (30), and other inputs and outputs described herein for monitoring and performing such processes and techniques. In one example, controller (46) has a processor configured to monitor user input provided via one or more inputs and capacitive touch sensors. Controller (46) may also include a touch screen controller to control and manage the acquisition of touch data from a capacitive touch screen.

Figure 2A:
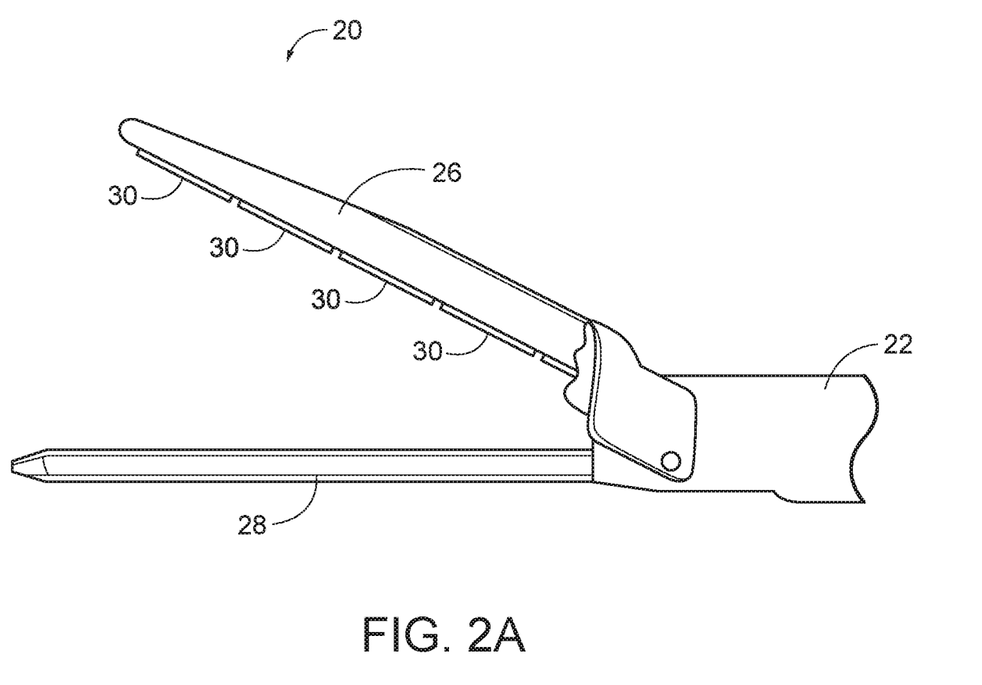
FIG. 2A depicts a side view of an end effector of the ultrasonic surgical instrument of FIG. 1 showing the end effector in an open configuration for receiving tissue of a patient.
Figure 2B:
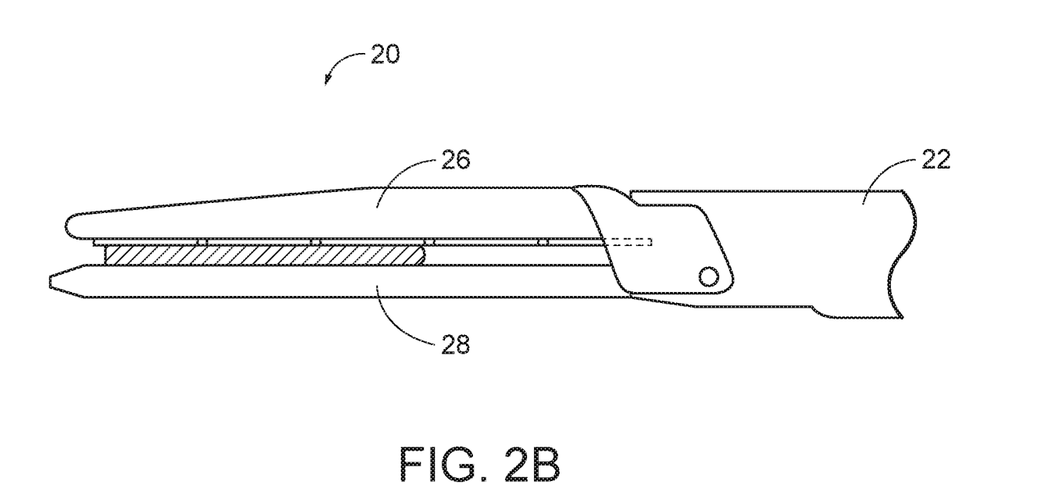
FIG. 2B depicts the side view of the end effector of FIG. 2A, but with the end effector in a closed configuration for clamping the tissue of the patient.

With reference to FIGS. 1-2B, handle assembly (18) further includes a trigger (48) operatively connected to clamp arm (26). Trigger (48) and clamp arm (26) are generally biased toward the unactuated, open configuration. However, selectively manipulating trigger (48) proximally pivots clamp arm (26) toward ultrasonic blade (28) from the open position to the closed position. As used in the present example, clamp arm (26) and ultrasonic blade (28) may also be generally referred to respectively as upper and lower jaws of surgical instrument (12). In the open position, clamp arm (26) and ultrasonic blade (28) are configured to receive the tissue, whereas clamp arm (26) is configured to clamp tissue against ultrasonic blade (28) for grasping, sealing, and/or cutting the tissue.

Ultrasonic blade (28) ultrasonically vibrates to seal and/or cut the tissue, whereas RF electrodes (30) provide electrical power to the tissue. RF electrodes (30) of the present example are all electrically similar electrodes with ultrasonic blade (28) also electrically connected as a return electrode. As used therein, the term "electrode" may thus apply to both RF electrodes (30) and ultrasonic blade (28) with respect to the RF electrical circuit. Without tissue, the electrical circuit from RF electrodes (30) to ultrasonic blade (28) is open, whereas the electrical circuit is closed by the tissue between RF electrode (30) and ultrasonic blade (28) in use. RF electrodes (30) may be activated to apply RF energy alone or in combination with ultrasonic activation of ultrasonic blade (28). For example, activating only RF electrodes (30) to apply RF energy alone may be used for spot coagulating without concern for inadvertently cutting tissue with ultrasonically activated ultrasonic blade (28). However, the combination of ultrasonic energy and RF energy may be used for sealing and/or cutting tissue to achieve any combination of diagnostic or therapeutic effects, various examples of which will be described below in greater detail.

As noted above, generator (14) is a single output generator that can deliver power through a single port to provide both RF and ultrasonic energy such that these signals can be delivered separately or simultaneously to end effector (20) for cutting and/or sealing tissue. Such a single output port generator (14) has a single output transformer with multiple taps to provide power, either for RF or for ultrasonic energy, to end effector (20) depending on the particular treatment being performed on the tissue. For example, generator (14) may deliver energy with higher voltage and lower current to drive ultrasonic transducer (24), with lower voltage and higher current as required to drive RF electrodes (30) for sealing tissue, or with a coagulation waveform for spot coagulation using either monopolar or bipolar electrosurgical electrodes. The output waveform from generator (14) can be steered, switched, or filtered to provide the desired frequency to end effector (20) of surgical instrument (12).

II. Sealing Tissue with Successive Energy Phase Application

Figure 3:
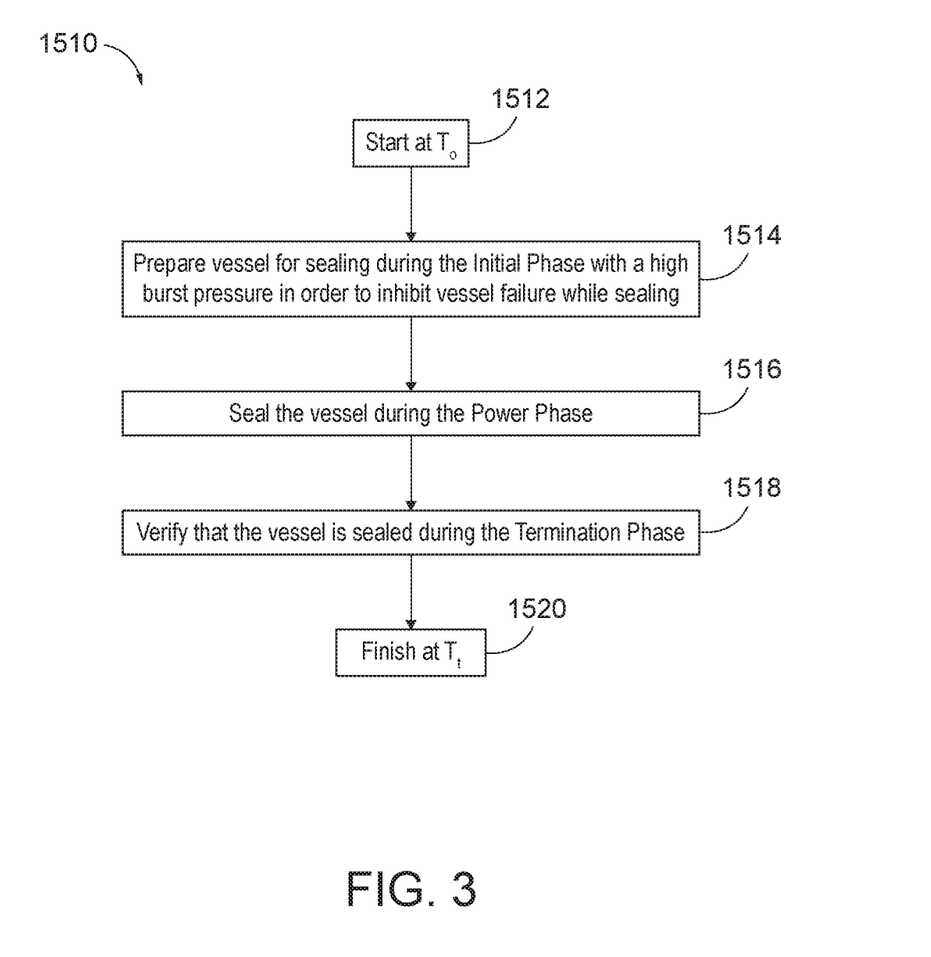
FIG. 3 depicts a high-level method of sealing tissue in successive phases.

FIG. 3 illustrates a high-level method (1510) of sealing tissue while inhibiting tissue transection by successively applying a variety of energy phases. To this end, ultrasonic and RF energies are applied to the tissue at an initial time, $T_o$, in a step (1512). The electrical parameters of the RF and ultrasonic energies are respectively configured to prepare the vessel for sealing by processing the tissue to have a high burst pressure in an initial phase step (1514), which generally inhibits vessel failure, also referred to herein as vessel transection. Following the initial phase step (514), a power phase step (516) seals the vessel while inhibiting transection of the vessel. A termination phase step (1518) then verifies that the vessel is sealed with additional processing that also continues to inhibit transection of the vessel. Finally, ultrasonic and RF energies are terminated at a termination time, $T_t$.

Figure 4A:
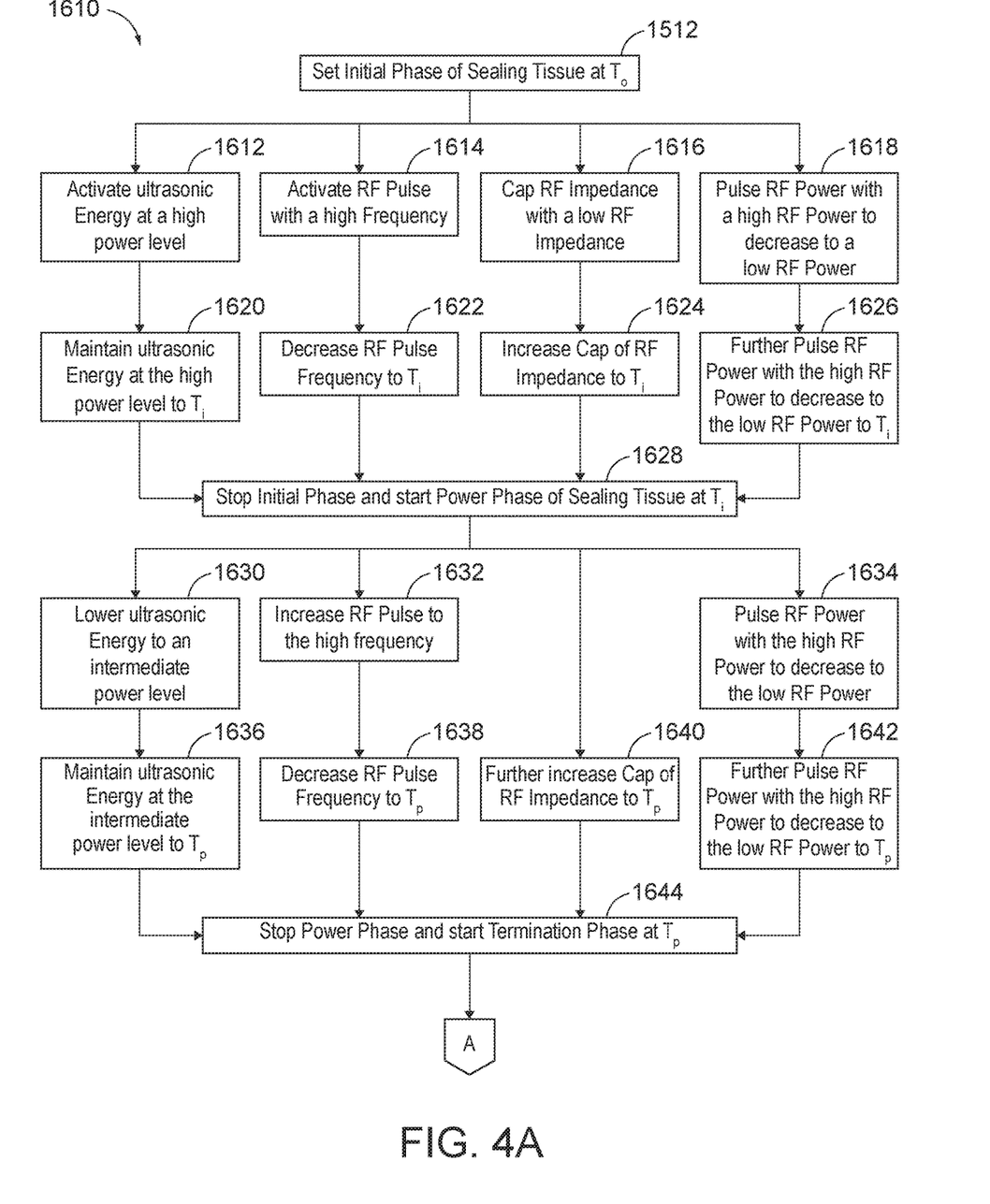
FIGS. 4A-4B depicts a version of the method of sealing tissue in successive phases of FIG. 3.
Figure 4B:
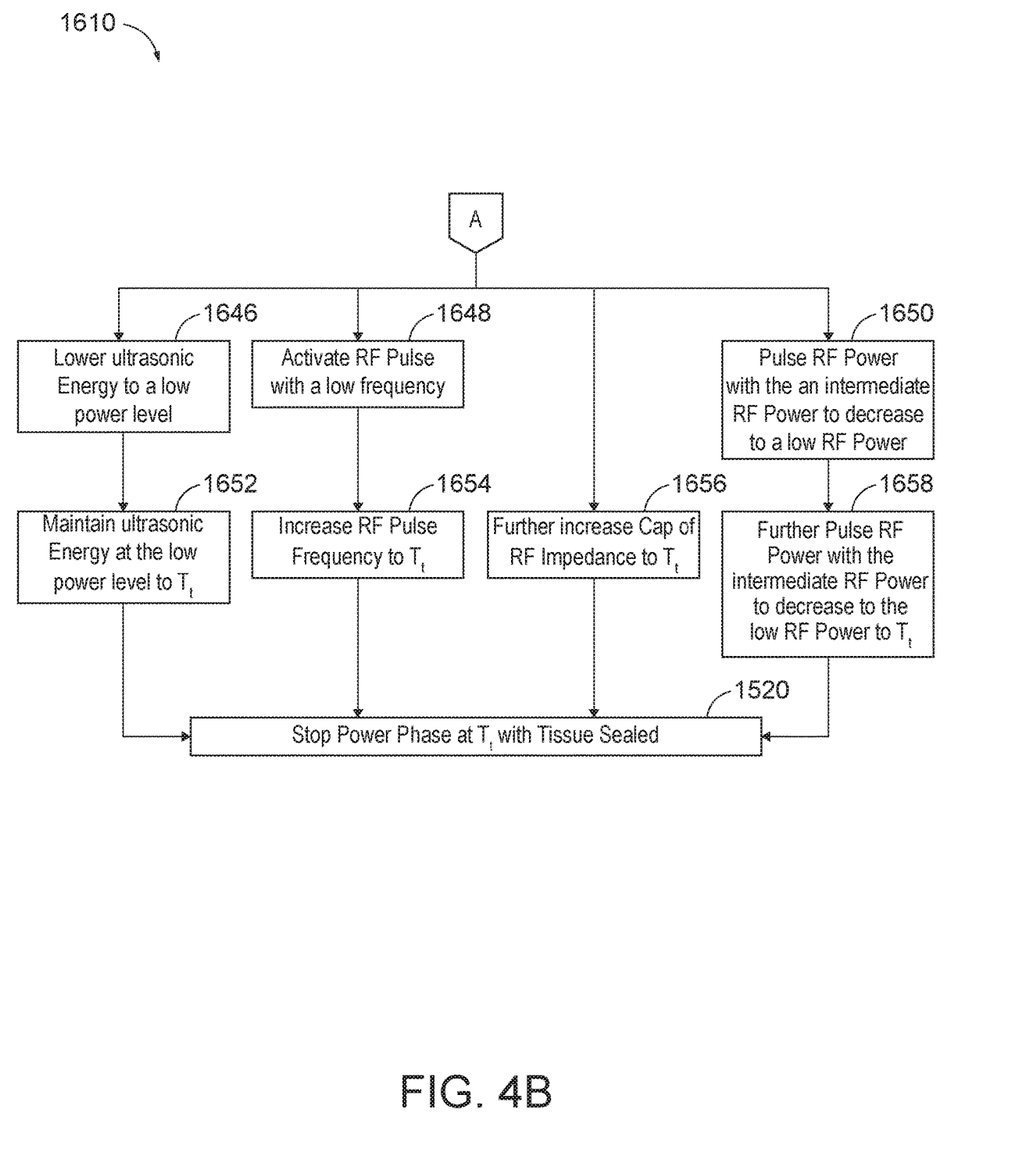
Figure 5:
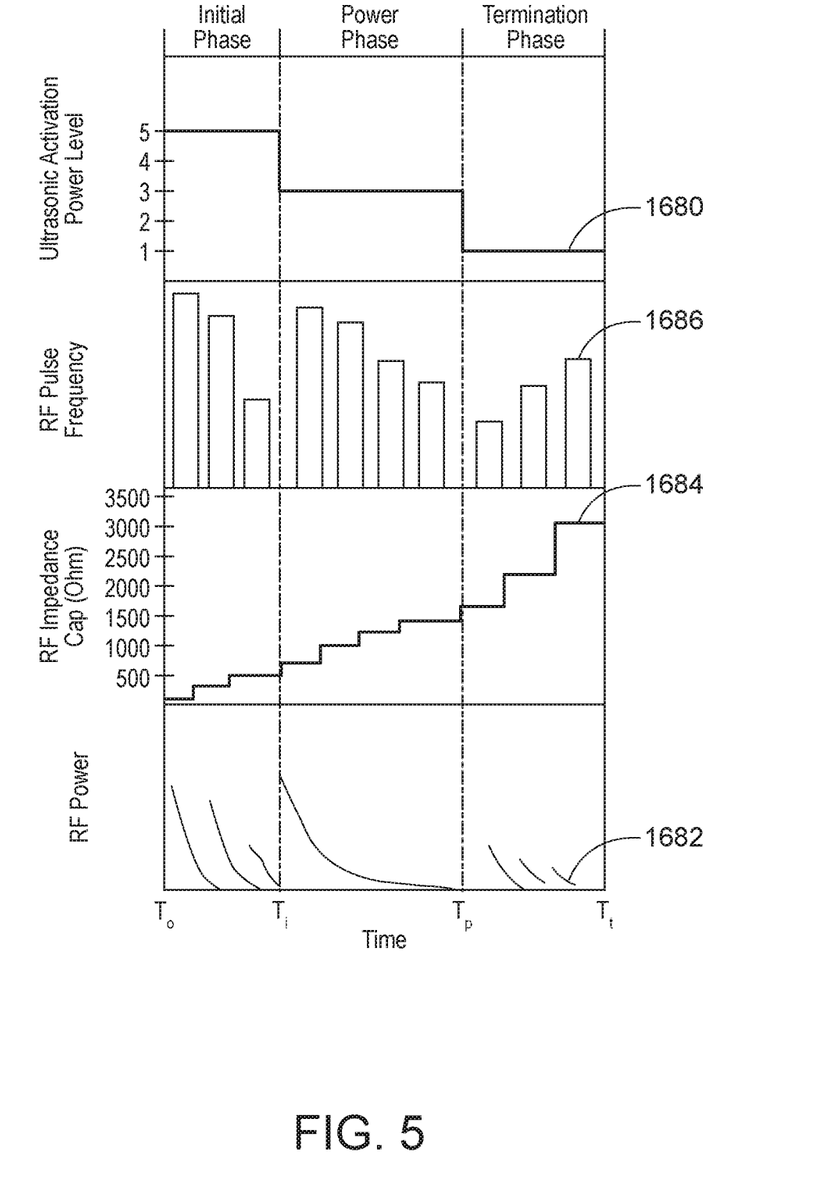
FIG. 5 depicts electrical parameters during the version of FIG. 4A-4B.

With respect to FIGS. 4A-4B and FIG. 5, one example of a version (1610) of high-level method (1510) (see FIG. 3) starts the initial phase of sealing tissue at the initial time, $T_o$, in step (1520). Exemplary parameters for ultrasonic energy in FIG. 5 include ultrasonic power (1680), and exemplary parameters for RF energy in FIG. 5 include RF power (1682), RF impedance (1684), and RF pulse frequency (1686). At the initial time, $T_o$, ultrasonic energy activates at a high power level in a step (1612), RF energy activates with pulses of a high frequency in a step (1614), RF impedance is capped with low RF impedance in a step (1616), and the pulsed RF power has a high RF power in a step (1618) that decreases to a low RF power. One such low RF impedance cap is from approximately 100 ohms to approximately 500 ohms. During the initial phase after the initial time, $T_o$, ultrasonic energy is maintained at the high power level until a time, $T_i$, in a step (1620), RF energy decreases pulse frequency until time, $T_i$, in a step (1622), the capped RF impedance increases to time, $T_i$, in a step (1624), and the pulsed RF power continues to decreases to the lower RF power to time, $T_i$, in a step (1626). Following step (1620) through (1626), the initial phase stops and the power phase starts at time, $T_i$. in a step (1628).

As the power phase of sealing the tissue begins at time, $T_i$, ultrasonic energy lowers to an intermediate power level in a step (1632), RF energy pulses increase to the high frequency in a step (1632), and RF power with the high RF power decreases to the low RF power in a step (1634). From the time, $T_i$, to the end of the power phase at a time, $T_p$, ultrasonic energy is maintained at the intermediate power level in a step (1636), RF pulse frequency decreases in a step (1638), RF impedance cap increases in a step (1648), and RF power is further pulsed with the high RF power that decreases to low RF power in a step (1642). One such RF impedance cap increases from approximately 500 ohms to approximately 1,500 ohms. Power phase thus stops in a step (1644), which also starts a termination phase at time, $T_p$.

The termination phase starts a time, $T_p$, with lowering the ultrasonic power level to a low power level in a step (1646), activating RF energy to pulse with a low frequency in a step (1648), and RF power pulses with an intermediate RF power that decreases to a low RF power in a step (1650). From the time, $T_p$, to the end of the power phase at a time, $T_t$, ultrasonic energy is maintained at the low power level in a step (1652), RF energy pulse frequency increases in a step (1654), the RF impedance cap increases in a step (1656), and RF power pulse decreases from the intermediate RF power to the lower RF power in a step (1658). One such RF impedance cap increases from approximately 1,500 ohms to approximately 2,000 ohms. At the time, $T_t$, the termination phase stops with the sealing of the tissue while inhibiting transection of the tissue and termination of the ultrasonic and RF energies in step (1520).

Figure 6:
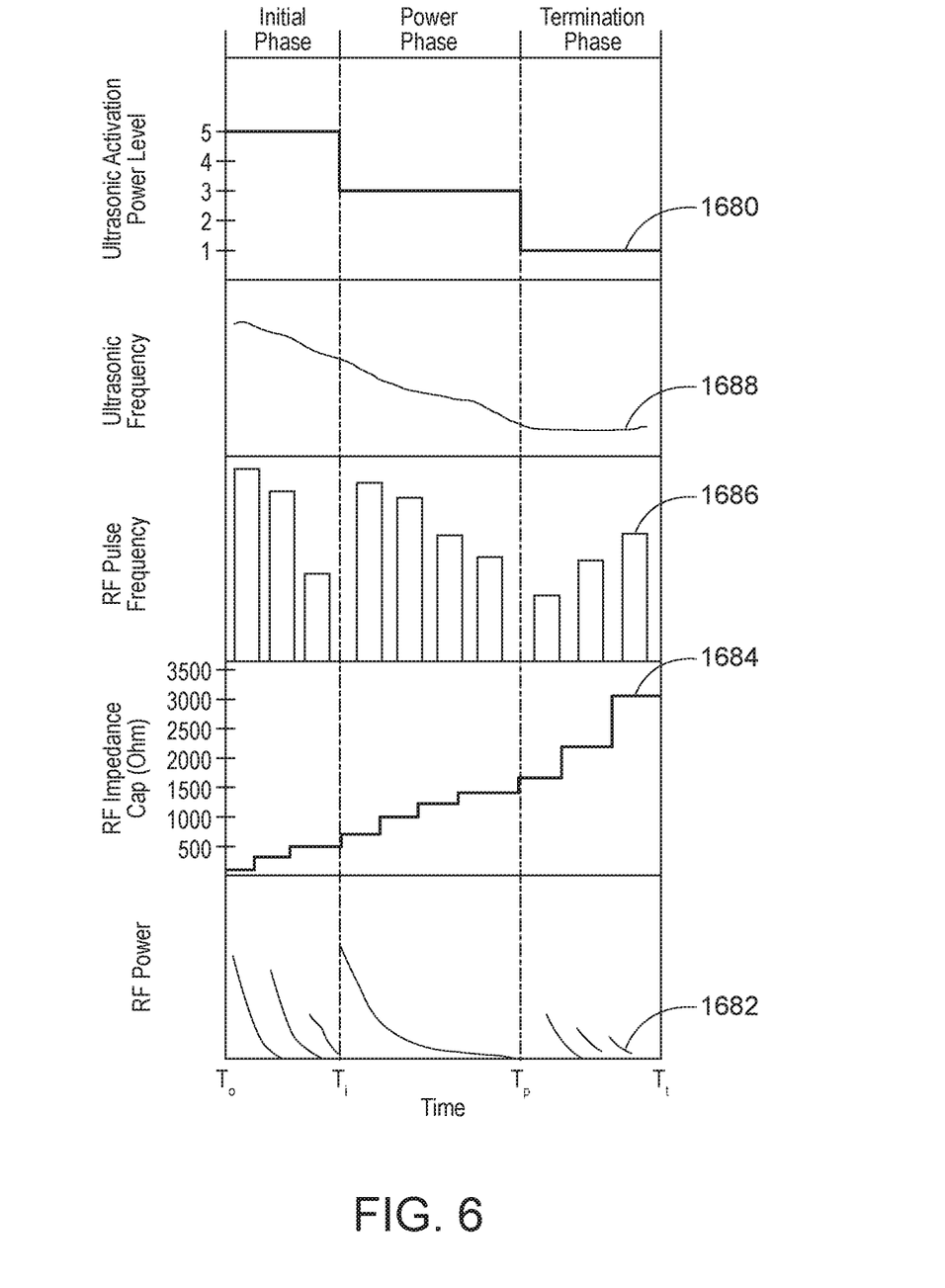
FIG. 6 depicts electrical parameters of another version of the method similar to FIG. 5, but with additional energy parameters.

While ultrasonic and RF energy parameters for the RF impedance cap, RF pulse frequency, and ultrasonic power level operate over time in constant step level functions, alternative versions may use one or more various level functions for greater accuracy and precision of operation. Furthermore, additional RF and/or ultrasonic energy parameters may be adjusted for sealing the tissue while inhibiting transection of the tissue. For example, another version of sealing the tissue shown in FIG. 6 operates generally as version (1610) discussed above, but ultrasonic energy has an additional parameter of an ultrasonic frequency (1688) with the ultrasonic energy frequency at the initial time, $T_0$, that is a high frequency that decreases continuously to a low frequency at the initiation of the termination phase at $T_p$. Through the termination phase from time, $T_p$, to the termination time, $T_t$, the ultrasonic energy frequency remains constant at the low frequency.

Figure 7:
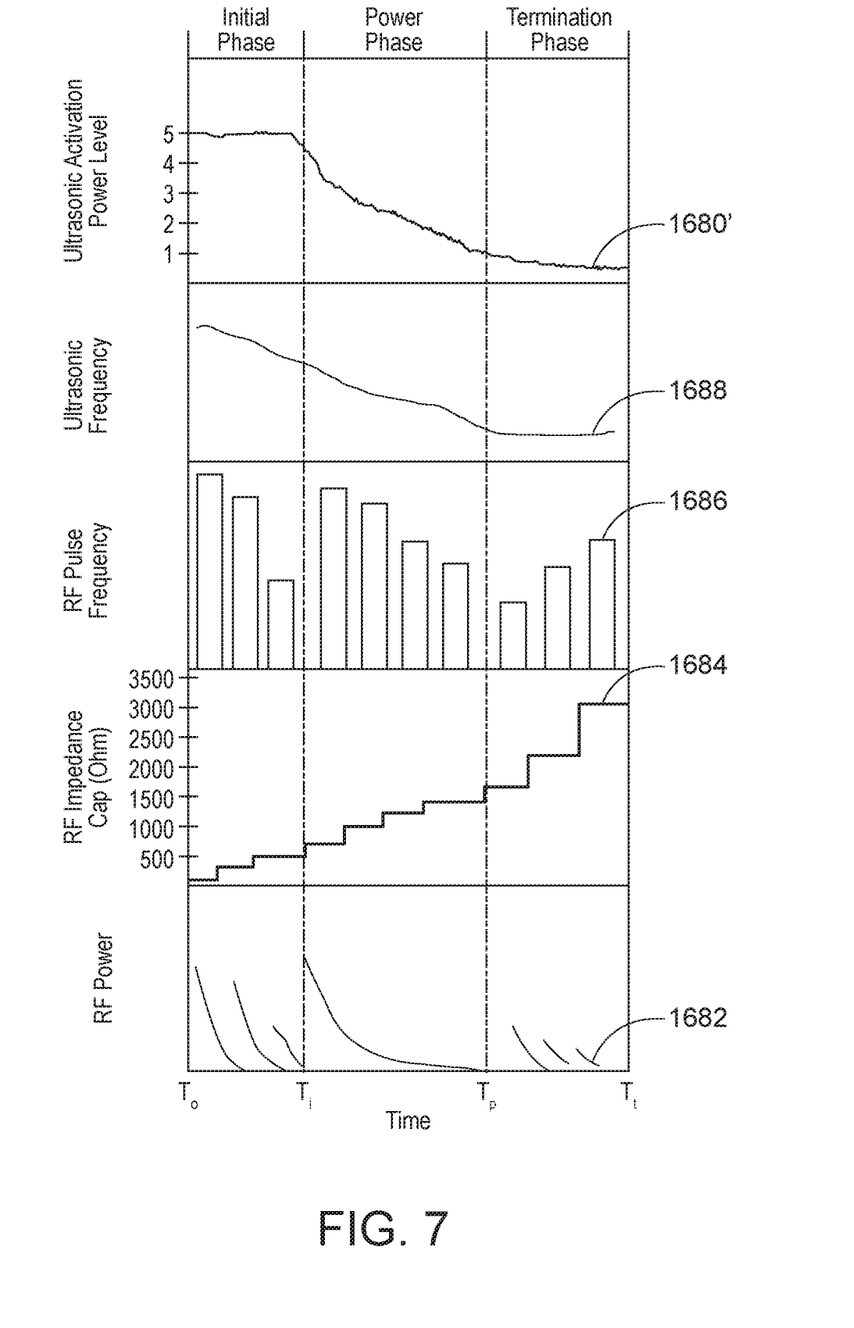
FIG. 7 depicts electrical parameters of yet another version of the method similar to FIG. 5, but with at least one additional variable function energy parameter.

Each of the above referenced phases is directed by controller (46) according to data tables, which are illustrated in FIGS. 4A-4B. By way of further example in FIG. 7, still another version of sealing the tissue operates generally as the version in FIG. 6, but has an alternative ultrasonic energy power level (1680') that remains constant at the high power level through the initial phase from the initial time, To, to time, $T_i$, but has an exponential decrease from the high power level to the low power level to termination at time, $T_t$. The invention is thus not intended to be unnecessarily limited to constant step level function or the electrical parameters described herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of sealing a tissue with a surgical instrument including a controller and an ultrasonic blade and an RF electrode respectively configured to deliver ultrasonic energy and RF energy to the tissue, wherein the controller is operatively connected to the ultrasonic blade and the RF electrode to direct application of the ultrasonic and RF energies, the method comprising: (a) activating the ultrasonic energy and the RF energy on the tissue; (b) generating a desired burst pressure in the tissue; (c) sealing the tissue; and (d) verifying that the tissue is sealed with further application of at least one of the ultrasonic energy or the RF energy.

Example 2

The method of Example 1, further comprising terminating the ultrasonic energy and the RF energy when the tissue is verified as sealed to thereby inhibit transecting the tissue.

Example 3

The method of Example 1, wherein generating the desired burse pressure in the tissue further includes generating the desired burst pressure in the tissue during an initial phase directed by the controller.

Example 4

The method of Example 3, further comprising: (a) activating the ultrasonic energy with a high power level in the initial phase; (b) activating an RF pulse frequency with a high frequency in the initial phase; (c) capping RF impedance with a low RF impedance in the initial phase; and (d) pulsing RF power with a high RF power toward a low RF power in the initial phase.

Example 5

The method of Example 4, further comprising: (a) maintaining the ultrasonic energy with the high power level in the initial phase after activating the ultrasonic energy with the high power level; (b) decreasing the RF pulse frequency from the high frequency in the initial phase after activating the RF pulse frequency with the high; (c) increasing the cap of the RF impedance from the capped low RF impedance in the initial phase after capping RF impedance with the low RF impedance; and (d) further pulsing RF power to the low RF power in the initial phase.

Example 6

The method of Example 1, wherein sealing the tissue further includes sealing the tissue during a power phase directed by the controller.

Example 7

The method of Example 6, further comprising: (a) activating the ultrasonic energy to an intermediate power level in the power phase; (b) activating the RF pulse frequency with a high frequency in the power phase; (c) capping RF impedance in the power phase; and (d) pulsing RF power with a high RF power toward a low RF power in the power phase.

Example 8

The method of Example 7, further comprising: (a) maintaining the ultrasonic energy at the intermediate power level in the power phase after activating the ultrasonic energy with the intermediate power level; (b) decreasing the RF pulse frequency from the high frequency in the power phase after activating the RF pulse frequency with the high frequency; (c) increasing the cap of the RF impedance in the power phase after capping RF impedance; and (d) further pulsing RF power to the low RF power in the power phase.

Example 9

The method of Example 1, wherein verifying that the tissue is sealed further includes verifying that the tissue is sealed with further application of at least one of the ultrasonic energy or the RF energy during a termination phase directed by the controller.

Example 10

The method of Example 9, further comprising: (a) activating the ultrasonic energy to a low power level in the termination phase; (b) activating the RF pulse frequency with a low frequency in the termination phase; (c) capping RF impedance in the termination phase; and (d) pulsing RF power with an intermediate RF power toward a low RF power in the termination phase.

Example 11

The method of Example 10, further comprising: (a) maintaining the ultrasonic energy at the low power level in the termination phase after activating the ultrasonic energy with the low power level; (b) increasing the RF pulse frequency from the low frequency in the termination phase after activating the RF pulse frequency with the low frequency; (c) increasing the cap of the RF impedance in the termination phase after capping RF impedance; and (d) further pulsing RF power to the low RF power in the termination phase.

Example 12

The method of Example 1, wherein generating the desired burst pressure in the tissue further includes generating the desired burst pressure in the tissue during an initial phase directed by the controller, wherein sealing the tissue further includes sealing the tissue during a power phase directed by the controller, and wherein verifying that the tissue is sealed further includes verifying that the tissue is sealed with further application of at least one of the ultrasonic energy or the RF energy during a termination phase directed by the controller.

Example 13

The method of Example 12, further comprising: (a) activating the ultrasonic energy with a high power level in the initial phase; (b) activating an RF pulse frequency with a high frequency in the initial phase; (c) capping RF impedance with a low RF impedance in the initial phase; and (d) pulsing RF power with a high RF power to a low RF power in the initial phase.

Example 14

The method of Example 13, further comprising: (a) lowering the ultrasonic energy to an intermediate power level in the power phase; (b) increasing the RF pulse frequency from a decreased frequency to the high frequency in the power phase; (c) increasing RF impedance cap in the power phase; and (d) pulsing RF power with the high RF power to the low RF power in the power phase.

Example 15

The method of Example 14, further comprising: (a) lowering the ultrasonic energy to a low power level in the termination phase; (b) decreasing the RF pulse frequency to the decreased frequency in the termination phase; (c) increasing RF impedance cap in the termination phase; and (d) pulsing RF power with an intermediate RF power to the low RF power in the termination phase.

Example 16

A method of sealing a tissue with a surgical instrument including a controller and an ultrasonic blade and an RF electrode respectively configured to deliver ultrasonic energy and RF energy to the tissue, wherein the controller is operatively connected to the ultrasonic blade and the RF electrode to direct application of the ultrasonic and RF energies, the method comprising: (a) generating a desired burst pressure in the tissue during an initial phase directed by the controller; and (b) sealing the tissue during a power phase directed by the controller.

Example 17

The method of Example 16, further comprising: (a) activating the ultrasonic energy with a high power level in the initial phase; (b) activating an RF pulse frequency with a high frequency in the initial phase; (c) capping RF impedance with a low RF impedance in the initial phase; and (d) pulsing RF power with a high RF power toward a low RF power in the initial phase.

Example 18

The method of Example 17, further comprising: (a) maintaining the ultrasonic energy with the high power level in the initial phase after activating the ultrasonic energy with the high power level; (b) decreasing the RF pulse frequency from the high frequency in the initial phase after activating the RF pulse frequency with the high; (c) increasing the cap of the RF impedance from the capped low RF impedance in the initial phase after capping RF impedance with the low RF impedance; and (d) further pulsing RF power to the low RF power in the initial phase.

Example 19

The method of Example 18, further comprising verifying that the tissue is sealed with further application of at least one of the ultrasonic energy or the RF energy during a termination phase directed by the controller.

Example 20

An ultrasonic surgical instrument, comprising: (a) an end effector configured to actuate from a first configuration to a second configuration, including: (i) an ultrasonic blade configured to apply ultrasonic energy to tissue, and (ii) an RF electrode configured to apply RF energy to tissue; (b) a shaft assembly projecting proximally from the end effector; (c) a body projecting proximally from the shaft assembly, wherein the body includes an energy input operatively connected to the ultrasonic blade; and (d) a controller operatively connected to the ultrasonic blade and the RF electrode, wherein the controller is configured to direct application of ultrasonic and RF energies to tissue via the ultrasonic blade and the RF electrode, respectively, according to an initial phase, a power phase, and a termination phase, wherein the controller in the initial phase is configured to power the ultrasonic blade and the RF electrode to generate a desired burst pressure in the tissue, wherein the controller in the power phase is configured to power the ultrasonic blade and the RF electrode to seal the tissue, and wherein the controller in the termination phase is configured to power the ultrasonic blade and the RF electrode to verify that the tissue is sealed while inhibiting transection of the tissue.

IV. Miscellaneous

It should be understood that any one or more of the teachings, expressions, embodiments, examples, etc.

described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of any claims.

Any one or more of the teaching, expressions, embodiments, examples, etc. described herein may be combined with any one or more of the teachings, expressions, embodiments, examples, etc. described in U.S. patent application Ser. No. 15/967,758, entitled "Combination Ultrasonic and Electrosurgical Instrument with Clamp Arm Position Input and Method for Identifying Tissue State," filed on May 1, 2018, published as U.S. Pub. No. 2018/0333182 on Nov. 22, 2018; U.S. patent application Ser. No. 15/967,763, entitled "Combination Ultrasonic and Electrosurgical Instrument with Adjustable Energy Modalities and Method for Sealing Tissue and Inhibiting Tissue Resection," filed on May 1, 2018, published as U.S. Pub. No. 2018/0333185 on Nov. 22, 2018; U.S. patent application Ser. No. 15/967,770, entitled "Combination Ultrasonic and Electrosurgical Instrument with Adjustable Clamp Force and Related Methods," filed on May 1, 2018, published as U.S. Pub. No. 2018/0333187 on Nov. 22, 201; U.S. patent application Ser. No. 15/967,775, entitled "Combination Ultrasonic and Electrosurgical Instrument with Adjustable Energy Modalities and Method for Limiting Blade Temperature," filed on May 1, 2018, published as U.S. Pub. No. 2018/0333188 on Nov. 22, 2018; and/or U.S. patent application Ser. No. 15/967,777, entitled "Combination Ultrasonic and Electrosurgical Instrument and Method for Sealing Tissue with Various Termination Parameters," filed on May 1, 2018, published as U.S. Pub. No. 2018/0333189 on Nov. 22, 2018. The disclosure of each of these applications is incorporated by reference herein.

Further, any one or more of the teachings, expressions, embodiments, examples, etc. described herein may be combined with any one or more of the teachings, expressions, embodiments, examples, etc. described in U.S. patent application Ser. No. 15/967,740, entitled "Combination Ultrasonic and Electrosurgical Instrument Having Electrical Circuits With Shared Return Path," filed on May 1, 2018, published as U.S. Pub. No. 2018/0333177 on Nov. 22, 2018; U.S. patent application Ser. No. 15/967,746, entitled "Combination Ultrasonic and Electrosurgical Instrument Having Slip Ring Electrical Contact Assembly," filed on May 1, 2018, issued as U.S. Pat. No. 10,945,778 on Mar. 16, 2021; U.S. patent application Ser. No. 15/967,747, entitled "Combination Ultrasonic and Electrosurgical Instrument Having Electrically Insulating Features," filed on May 1, 2018, issued as U.S. Pat. No. 10,945,779 on Mar. 16, 2021; U.S. patent application Ser. No. 15/967,751, entitled "Combination Ultrasonic and Electrosurgical Instrument Having Curved Ultrasonic Blade," filed on May 1, 2018, issued as U.S. Pat. No. 11,033,316 on Jun. 15, 2021; U.S. patent application Ser. No. 15/967,753, entitled "Combination Ultrasonic and Electrosurgical Instrument Having Clamp Arm Electrode," filed on May 1, 2018, issued as U.S. Pat. No. 11,058,472 on Jul. 13, 2021; U.S. patent application Ser. No. 15/967,759, entitled "Combination Ultrasonic and Electrosurgical Instrument Having Ultrasonic Waveguide With Distal Overmold Member," filed on May 1, 2018, issued as U.S. Pat. No. 11,051,866 on Jul. 6, 2021; U.S. patent application Ser. No. 15/967,761, entitled "Combination Ultrasonic and Electrosurgical System Having Generator Filter Circuitry," filed on May 1, 2018, published as U.S. Pub. No. 2018/0333184 on Nov. 22, 2018; and/or U.S. patent application Ser. No. 15/967,764, entitled "Combination Ultrasonic and Electrosurgical System Having EEPROM and ASIC Components," filed on May 1, 2018, issued as U.S. Pat. No. 11,129,661 on Sep. 28, 2021. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a clinician immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention is understood not to be limited to the details of structure and operation shown and described in the specification and drawings.

We claim:

1. A method of sealing a tissue with a surgical instrument including a controller and an ultrasonic blade and a radiofrequency (RF) electrode respectively configured to deliver ultrasonic energy and RF energy to the tissue, wherein the controller is operatively connected to the ultrasonic blade and the RF electrode to direct application of the ultrasonic energy and the RF energy, the method comprising:
    (a) activating the ultrasonic energy and the RF energy on the tissue, wherein the ultrasonic energy is activated with a high power level in an initial phase directed by the controller;
    (b) generating a desired burst pressure in the tissue during the initial phase;
    (c) activating the ultrasonic energy to an intermediate power level in a power phase directed by the controller, wherein the power phase occurs after the initial phase;
    (d) sealing the tissue during the power phase directed by the controller;
    (e) activating the ultrasonic energy to a low power level in a termination phase directed by the controller, wherein the termination phase occurs after the power phase; and
    (f) verifying that the tissue is sealed with further application of at least one of the ultrasonic energy or the RF energy during the termination phase.

2. The method of claim 1, further comprising terminating the ultrasonic energy and the RF energy when the tissue is verified as sealed to thereby inhibit transecting the tissue.

3. The method of claim 1, further comprising:
    (a) activating an RF pulse frequency with a high frequency in the initial phase;
    (b) capping RF impedance with a low RF impedance in the initial phase; and
    (c) pulsing RF power with a high RF power toward a low RF power in the initial phase.

4. The method of claim 3, further comprising:
    (a) maintaining the ultrasonic energy with the high power level in the initial phase after activating the ultrasonic energy with the high power level;
    (b) decreasing the RF pulse frequency from the high frequency in the initial phase after activating the RF pulse frequency with the high frequency;
    (c) increasing the cap of the RF impedance from the capped low RF impedance in the initial phase after capping RF impedance with the low RF impedance; and
    (d) further pulsing RF power to the low RF power in the initial phase.

5. The method of claim 1, further comprising:
    (a) activating the RF pulse frequency with a high frequency in the power phase;
    (b) capping RF impedance in the power phase; and
    (c) pulsing RF power with a high RF power toward a low RF power in the power phase.

6. The method of claim 5, further comprising:
    (a) maintaining the ultrasonic energy at the intermediate power level in the power phase after activating the ultrasonic energy with the intermediate power level;

(b) decreasing the RF pulse frequency from the high frequency in the power phase after activating the RF pulse frequency with the high frequency;
(c) increasing the cap of the RF impedance in the power phase after capping RF impedance; and
(d) further pulsing RF power to the low RF power in the power phase.

7. The method of claim 1, further comprising:
(a) activating the RF pulse frequency with a low frequency in the termination phase;
(b) capping RF impedance in the termination phase; and
(c) pulsing RF power with an intermediate RF power toward a low RF power in the termination phase.

8. The method of claim 7, further comprising:
(a) maintaining the ultrasonic energy at the low power level in the termination phase after activating the ultrasonic energy with the low power level;
(b) increasing the RF pulse frequency from the low frequency in the termination phase after activating the RF pulse frequency with the low frequency;
(c) increasing the cap of the RF impedance in the termination phase after capping RF impedance; and
(d) further pulsing RF power to the low RF power in the termination phase.

9. The method of claim 1, further comprising:
(a) activating an RF pulse frequency with a high frequency in the initial phase;
(b) decreasing the RF pulse frequency from the high frequency to a decreased frequency;
(c) capping RF impedance with a low RF impedance in the initial phase; and
(d) pulsing RF power with a high RF power to a low RF power in the initial phase.

10. The method of claim 9, further comprising:
(a) increasing the RF pulse frequency from the decreased frequency in the power phase;
(b) increasing RF impedance cap in the power phase; and
(c) pulsing RF power with the high RF power to the low RF power in the power phase.

11. The method of claim 10, further comprising:
(a) decreasing the RF pulse frequency in the termination phase;
(b) increasing RF impedance cap in the termination phase; and
(c) pulsing RF power with an intermediate RF power to the low RF power in the termination phase.

12. The method of claim 1, further comprising increasing an RF pulse frequency from a first frequency in the initial phase to a second frequency in the power phase.

13. The method of claim 12, further comprising decreasing the RF pulse frequency from the second frequency in the power phase.

14. The method of claim 1, wherein the ultrasonic energy in the initial phase has a first ultrasonic frequency, wherein the ultrasonic energy in the power phase has a second ultrasonic frequency, and wherein the first ultrasonic frequency is higher than the second ultrasonic frequency.

15. A method of sealing a tissue with a surgical instrument including a controller and an ultrasonic blade and a radiofrequency (RF) electrode respectively configured to deliver ultrasonic energy and RF energy to the tissue, wherein the controller is operatively connected to the ultrasonic blade and the RF electrode to direct application of the ultrasonic energy and the RF energy, the method comprising:
(a) generating a desired burst pressure in the tissue during an initial phase directed by the controller;
(b) activating an RF pulse frequency with a first RF frequency in the initial phase
(c) activating the ultrasonic energy with a first ultrasonic frequency in the initial phase;
(d) decreasing the RF pulse frequency from the first RF frequency in the initial phase to a second RF frequency in the initial phase after activating the RF pulse frequency with the first RF frequency in the initial phase;
(e) decreasing the first ultrasonic frequency in the initial phase while a power level of the ultrasonic energy in the initial phase remains constant;
(f) increasing the RF pulse frequency from the second RF frequency in the initial phase toward a third RF frequency in a power phase; and
(g) sealing the tissue during the power phase directed by the controller.

16. The method of claim 15, further comprising:
(a) activating the ultrasonic energy with a high power level in the initial phase;
(b) capping RF impedance with a low RF impedance in the initial phase; and
(c) pulsing RF power with a high RF power toward a low RF power in the initial phase.

17. The method of claim 16, further comprising:
(a) maintaining the ultrasonic energy with the high power level in the initial phase after activating the ultrasonic energy with the high power level;
(b) increasing the cap of the RF impedance from the capped low RF impedance in the initial phase after capping RF impedance with the low RF impedance; and
(c) further pulsing RF power to the low RF power in the initial phase.

18. The method of claim 17, further comprising verifying that the tissue is sealed with further application of at least one of the ultrasonic energy or the RF energy during a termination phase directed by the controller.

19. A method of sealing a tissue with a surgical instrument including a controller and an ultrasonic blade and a radiofrequency (RF) electrode respectively configured to deliver ultrasonic energy and RF energy to the tissue, wherein the controller is operatively connected to the ultrasonic blade and the RF electrode to direct application of the ultrasonic energy and the RF energy, the method comprising:
(a) activating the ultrasonic energy and the RF energy on the tissue during an initial phase directed by the controller, wherein the ultrasonic energy has a first ultrasonic frequency in the initial phase;
(b) generating a desired burst pressure in the tissue during the initial phase;
(c) activating the ultrasonic energy with a second ultrasonic frequency in a power phase directed by the controller, wherein the first ultrasonic frequency is higher than the second ultrasonic frequency, and wherein the power phase is after the initial phase; and
(d) sealing the tissue during the power phase.

20. The method of claim 19, further comprising decreasing the first ultrasonic frequency of the ultrasonic energy in the initial phase while a power level of the ultrasonic energy in the initial phase remains constant.

* * * * *